US 6,565,653 B2

(12) United States Patent
Wilsak

(10) Patent No.: US 6,565,653 B2
(45) Date of Patent: May 20, 2003

(54) ENERGY EFFICIENT PROCESS FOR PRODUCING HIGH PURITY PARAXYLENE

(75) Inventor: Richard A. Wilsak, Naperville, IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 10/025,153

(22) Filed: Dec. 18, 2001

(65) Prior Publication Data
US 2002/0185056 A1 Dec. 12, 2002

Related U.S. Application Data
(60) Provisional application No. 60/289,313, filed on May 8, 2001.

(51) Int. Cl.[7] ............................................. C30B 7/00
(52) U.S. Cl. ...................... 117/68; 422/245.1; 585/412
(58) Field of Search ............................. 585/812, 828; 422/245.1; 117/68

(56) References Cited

U.S. PATENT DOCUMENTS

| 3,770,841 A | 11/1973 | Meyers, Jr. ............ 260/668 A |
| 5,448,005 A | 9/1995 | Eccli et al. ................. 585/812 |
| 5,811,629 A | 9/1998 | Hubbell et al. ............. 585/815 |
| 5,948,950 A | 9/1999 | Hotier et al. ............... 585/828 |
| 6,111,161 A | 8/2000 | MacPherson et al. ....... 585/812 |
| 6,147,272 A | 11/2000 | Mikitenko et al. .......... 585/812 |

FOREIGN PATENT DOCUMENTS

| FR | 2739097 | 9/1996 |
| GB | 1420796 | 1/1976 |

Primary Examiner—Felisa Hiteshew
(74) Attorney, Agent, or Firm—Mary Jo Kanady; Thomas A. Yassen

(57) ABSTRACT

The invention is a novel energy efficient process to produce high purity paraxylene from a feed comprising at least 55 to 60 wt % paraxylene, wherein a first portion of high purity paraxylene product is obtained in a first crystallization step at about 10° F. to about 55° F. without the need for further reslurry and recrystallization, and wherein another portion of the high purity paraxylene product is obtained following a reslurry step which warms crystalline paraxylene obtained from subsequent lower temperature crystallizations to yield a slurry at a temperature of about 10° F. to about 55° F. without the need for further refrigeration.

66 Claims, 3 Drawing Sheets

ENERGY EFFICIENT PROCESS FOR PRODUCING HIGH PURITY PARAXYLENE

This application claims the benefit of U.S. Provisional Application No. 60/289,313 filed May 8, 2001, which is incorporated herein by reference in its entirety.

FIELD OF THE INVENTION

The present invention relates to a novel energy efficient process for the production of high purity paraxylene (pX) from a feedstock of $C_8$ aromatics which preferably comprises at least about 60 weight percent (wt %) paraxylene wherein a first portion of high purity paraxylene product is obtained in a first crystallization step at a temperature of from about 10° F. to about 55° F. followed by separation of the washed paraxylene crystals without the need for further reslurry and recrystallization and wherein another portion of the high purity paraxylene product is obtained following a reslurry step that warms crystalline paraxylene obtained from subsequent lower temperature crystallizations to yield a slurry at a temperature of from about 10° F. to about 55° F. without the need for further refrigeration. The paraxylene crystals are separated from the slurry mother liquor to give high purity paraxylene product. In an alternate embodiment of the invention, the feedstock may comprise at least about 55 weight percent paraxylene.

BACKGROUND OF THE INVENTION

The separation of xylene isomers has been of particular interest because of the usefulness of para-xylene in the manufacture of terephthalic acid which is used in the manufacture of polyester fabric. Paraxylene is a chemical intermediate useful for the manufacture of terephthalic acid, the major constituent of polyethylene terephthalate. Paraxylene having a purity of at least about 99.5, more preferably of at least about 99.7 weight percent, is used to manufacture terephthalic acid by the oxidation of paraxylene. Other components of the $C_8$ aromatic hydrocarbon feedstream from which para-xylene (pX) is generally produced are ortho-xylene (oX), which is used in the manufacture of phthalic anhydride which is used to make phthalate based plasticizers; meta-xylene (mX), which is used in the manufacture of isophthalic acid used in the production of specialty polyester fibers, paints, and resins; and ethylbenzene (EB) which is used in the manufacture of styrene.

A refinery feedstock of aromatic $C_8$ mixtures containing ethylbenzene and xylenes will typically have the following content:

| | |
|---|---|
| ethylbenzene | about 0 wt % to about 50 wt % |
| para-xylene | about 0 wt % to about 25 wt % |
| ortho-xylene | about 0 wt % to about 35 wt % |
| meta-xylene | about 20 wt % to about 90 wt % |
| non-aromatics | about 0 wt % to about 10 wt % |
| $C_9^+$ aromatics | about 0 wt % to about 30 wt % |

Equilibrium mixtures of $C_8$ aromatic hydrocarbons generally contain about 22 weight percent para-xylene, about 21 weight percent ortho-xylene, and about 48 weight percent meta-xylene.

Processes to separate xylene isomers include low temperature crystallization, fractional distillation, selective sulfonation with subsequent hydrolysis and selective solvent separation; however, such processes require high operating costs.

Crystallization can be used to separate paraxylene from a $C_8$ aromatic feedstream comprising paraxylene, meta-xylene, ortho-xylene, and ethylbenzene due to the fact that the components have different melting points. Paraxylene freezes at 13° C., meta-xylene freezes at −48° C., ortho-xylene freezes at −25° C., and ethylbenzene freezes at −95° C.

Crystallization has been used commercially to isolate and purity paraxylene, typically from a mixture of xylenes and ethylbenzene close to chemical equilibrium. Because of the low concentration of paraxylene in these mixed xylene streams, very low temperatures are generally required to effectively recover the paraxylene from a $C_8$ fraction by crystallization. Furthermore, there is an operational low temperature limit generally taken as the meta-xylene/paraxylene or the ortho-xylene/paraxylene binary eutectic temperature that prevents the complete recovery of all the paraxylene from a $C_8$ fraction. At or below this limit, either meta-xylene or ortho-xylene will co-crystallize with paraxylene. The use of such low temperatures for crystallization is expensive and requires a substantial use of energy. There is a need for a more energy efficient process for crystallizing and purifying paraxylene from a feed containing paraxylene and other $C_8$ aromatics.

U.S. Pat. No. 6,111,161 discloses a process for the production of high purity paraxylene from a charge containing $C_7$–$C_9$ aromatic hydrocarbons in which a first fraction is enriched to at least 30% weight with paraxylene and this fraction is purified by at least one high-temperature crystallization in at least one crystallization zone. Said first fraction is crystallized in a crystallization zone at high temperature T1 and advantageously between +10 and −25° C. Crystals in suspension in a mother liquor are recovered, and the crystals are separated from the mother liquor in at least a first separation zone. The crystals obtained are partially melted in at least a zone for partial melting and a suspension of crystals is recovered. The crystals in suspension are separated and washed in at least one separation and washing zone and pure paraxylene crystals and washing liquor are recovered, and pure crystals are optionally completely melted and a liquid stream of melted paraxylene is collected.

U.S. Pat. No. 5,448,005 discloses a process for producing high purity paraxylene from a high weight percent paraxylene feedstock, comprising at least about 70 wt % paraxylene and preferably at least about 80 wt % paraxylene which uses a single temperature crystallization production stage at a temperature in the range of from about 0° F. to about 50° F. and also uses scavenger stages to raise the paraxylene recovery rate. The single temperature production stage crystallizer of the process employs a wash using only paraxylene product.

The present invention has an advantage over other crystallization processes. It reduces the refrigeration requirements compared to designs disclosed in U.S. Pat. Nos. 6,111,161 and 5,448,005. Thus, it requires less energy expenditure and provides a cost savings compared to those designs. It accomplishes this by separating some or most of the final product early in the separation sequence, thereby reducing the amount of material that requires lower temperature refrigeration. It does not recycle cake back to the first crystallizer from the lower temperature stage(s), but rather uses a reslurry drum to sufficiently warm the crystals so that additional para-xylene product can be recovered without the need for more refrigeration. As calculated according to standard engineering practices, the refrigeration compressor horsepower for the invention can be as much as 13% less than that for comparable designs based on the teachings of U.S. Pat. No. 6,111,161.

SUMMARY OF THE INVENTION

The present invention relates to a process for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of from about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting the liquid paraxylene product;

d) transferring at least a portion of filtrate from the first separation unit to a second crystallizer which is operated at a temperature lower than that of the first crystallizer, crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature higher than that of the lowest temperature crystallizer;

i) separating the slurry mixture in a fourth separation unit to produce a filtrate and a crystalline paraxylene product, washing the paraxylene crystals with liquid paraxylene, completely melting the paraxylene crystals, and collecting the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

Preferably, the crystalline paraxylene product from step (c) is combined with the crystalline paraxylene product from step (i) prior to melting. This can be suitably accomplished by sending the two paraxylene products to the same melt drum.

The present invention also relates to a process for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of from about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of from about −10° F. to about 35° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of from about −35° F. to about 5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of from about 10° F. to about 55° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

The present invention additionally relates to a process for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of from about 30° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of from about 15° F. to about 25° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer which is operated at a temperature of from about −10° F. to about −5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of from about 30° F. to about 50° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

The present invention also relates to a process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of from about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting the liquid paraxylene product;

d) transferring at least a portion of filtrate from the first separation unit to a second crystallizer which is operated at a temperature lower than that of the first crystallizer, crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature higher than that of the lowest temperature crystallizer;

i) separating the slurry mixture in a fourth separation unit to produce a filtrate and a crystalline paraxylene product, washing the paraxylene crystals with liquid paraxylene, completely melting the paraxylene crystals, and collecting the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

The present invention additionally relates to a process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of from about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of from about −10° F. to about 35° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of from about −35° F. to about 5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of from about 10° F. to about 55° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

The present invention additionally relates to a process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of from about 20° F. to about 30° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of from about 5° F. to about 15°

F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of from about −10° F. to about −5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of from about 30° F. to about 50° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

In the process of the invention, the crystalline paraxylene product produced in step (c) is conveniently combined with the crystalline paraxylene product produced in step (i) in a melt drum or other suitable melting means and melted to give a high purity liquid paraxylene product.

A portion of the high purity liquid paraxylene product is preferably used to wash the crystalline paraxylene obtained in steps (c) and (i). The ratio of wash to crystalline paraxylene is suitably about 0.10:1 to about 0.5:1 by weight, more preferably about 0.2:1 to about 0.35:1 by weight. A preferable source of paraxylene for the washing of the purified crystalline paraxylene is the purified liquid paraxylene product produced by the process of this invention.

The slurry mixture formed by mixing the paraxylene crystals obtained from the second and third crystallizations with paraxylene-containing liquid may also be referred to as a reslurry mixture since the paraxylene crystals will have come out of the second and third crystallizers in a slurry with mother liquor prior to separation and are being contacted with paraxylene-containing liquid in a slurry vessel or slurry apparatus to form another slurry. It is preferable to stir or mix the slurry mixture with, for example, a suitable mechanical agitator apparatus. The slurry mixture is maintained in the slurry apparatus (which may also be referred to as a slurry vessel or reslurry drum) for a time sufficient to increase the purity of the crystalline paraxylene contained therein to the desired purity. For the preferred continuous process of this invention, the residence time for the slurry in the slurry vessel is typically about 0.2 to about 2 hours, more preferably about 0.5 to about 1 hour.

Paraxylene produced in the process of the invention has a purity of about 99.5 wt % paraxylene or greater, preferably about 99.7 wt % paraxylene or greater; and most preferably about 99.8 wt % paraxylene or greater.

DESCRIPTION OF THE PREFERRED EMBODIMENT(S)

The present invention relates to an energy efficient process for recovering a high purity paraxylene product from a feedstream comprising paraxylene in a concentration greater than that found in equilibrium mixtures of $C_8$ aromatics. Preferably, the feedstream will comprise at least about 60 weight percent paraxylene. The feedstream may also comprise other $C_7$ to $C_9$ aromatic compounds, including orthoxylene, meta-xylene, and ethylbenzene. The process is based on two concepts which together provide an advantage over other known processes. The first concept centers on the first stage of crystallization and separation. By the appropriate choice of process conditions and equipment, the first stage is capable of producing high purity product that does not require further processing. This improves efficiency and cost effectiveness compared to other crystallization processes which recycle and recrystallize the paraxylene before obtaining the final product. The second concept centers on the use of reslurry technology to warm all of the crystalline paraxylene cake that is too cold to conveniently yield high purity paraxylene product directly but, most importantly, requires no refrigeration and, therefore, reduces energy requirements and cost. A reslurry drum is used to warm the paraxylene crystals that are obtained from low temperature crystallizers that are too cold to make paraxylene product directly or conveniently. If the paraxylene crystals are too cold, the paraxylene wash used to displace the impure mother liquor in the cake will freeze and not penetrate the cake.

The crystallization process of the present invention can be used in combination with any process that yields a stream containing at least about 60 weight percent (wt %) paraxylene, preferably greater than about 60 wt % paraxylene, more preferably at least about 70 wt % paraxylene, more preferably at least about 75 wt % paraxylene, more preferably at least about 80 wt % paraxylene, more preferably at least about 85 wt % paraxylene, more preferably at least about 90 wt % paraxylene, and most preferably at least about 95 wt % paraxylene, to produce a high purity paraxylene product. In one embodiment of the invention, the feedsteam can contain at least about 55 wt % paraxylene.

Paraxylene produced in the process of the invention has a purity of about 99.5 wt % paraxylene or greater, preferably about 99.7 wt % paraxylene or greater, more preferably about 99.8 wt % paraxylene or greater.

Figure 1:
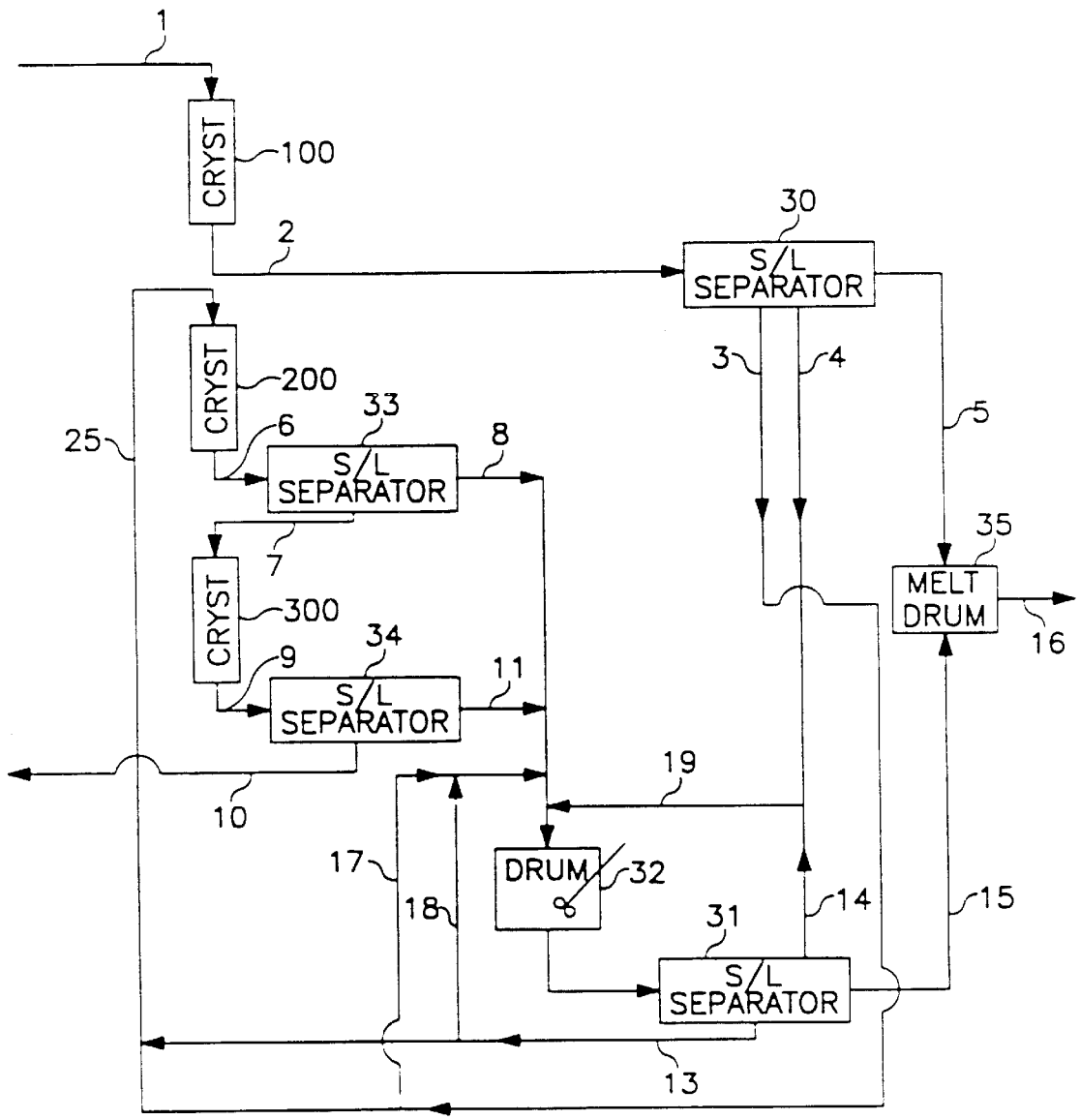
FIG. 1 shows a schematic of an embodiment of the present invention in which three crystallization steps and one reslurry step are used and in which at least a portion of the reject filtrate from the separation of the effluent from the reslurry drum is recycled to the second crystallization step. High purity paraxylene product is obtained from the first crystallization step without being subjected to recycling or recrystallization.

An embodiment of the present invention is illustrated in FIG. 1. In the following discussions, when referring to the drawings, the stream number corresponds to the number of the line in which the stream is transported. A paraxylene-containing feed is passed through line 1 to at least one high temperature crystallizer 100 where it is cooled to a temperature sufficient to crystallize paraxylene without crystallizing meta-xylene and ortho-xylene. Preferably, the feed in line 1 (stream 1) will comprise at least about 60 wt % paraxylene. Stream 1 may be obtained from any appropriate source which can produce a feed containing about 60 wt % paraxylene. For example, it could come from an adsorption process such as a HYSORB™ unit made by UOP; it could come from a pressure swing adsorption (PSA) unit; it could come from a reaction process such as a toluene disproportionation (TDP) unit; or it could come from another crystallization process such as a low temperature crystallization stage. Various feeds having the same or different paraxylene compositions can also be combined to provide the feed for the process of the present invention. It is desirable that the composition of stream 1 be at least about 60 weight percent paraxylene, preferably greater than about 60 wt % paraxylene, more preferably at least about 70 wt % paraxylene, more preferably at least about 75 wt % paraxylene, more preferably at least about 80 wt % paraxylene, more preferably at least about 85 wt % paraxylene, more preferably at least about 90 wt % paraxylene, more preferably greater than about 90 wt % paraxylene, still more preferably at least about 95 wt % paraxylene.

A $C_8$ aromatic stream comprising at least about 60 wt % paraxylene (stream 1) is fed via line 1 to a high temperature crystallizer 100 which is at a temperature of about 10° F. to about 55° F., preferably from about 30° F. to about 55° F. producing an effluent in line 2 (stream 2) comprising a slurry of paraxylene crystals and mother liquor which is conveyed via line 2 to a liquid-solid separation unit 30 which is operated at a temperature sufficiently low to maintain the crystalline paraxylene in the crystalline state. No refrigeration is needed to maintain this operating temperature. The conditions of stream 2 will vary depending on the composition of stream 1. For an embodiment in which stream 1 contains about 90 wt % paraxylene, the temperature of the effluent stream (stream 2) in line 2 may be about 40° F. In the present invention, the crystallizers are preferably all operated at about atmospheric pressure; however, by this is meant that sufficient pressure is maintained inside the crystallizer to prevent the entry of air in the event of a leak. Therefore, in operation, the crystallizer chamber will usually be maintained at slightly above atmospheric pressure. This is less costly than operating under pressure which requires thicker walls and stronger flanges to handle the increased pressure.

The crystallizer 100 to which the $C_8$ aromatic stream 1 is fed can comprise various numbers and types of crystallization devices in various sequences as is known to those skilled in the art. For example, a single crystallization device can be used or multiple units may be used. If multiple units are used, the crystallization vessels can be arranged in parallel, in series, or in other more complex configurations. There are various types of crystallization devices available, such as draft tube crystallizers and scraped wall crystallizers. The type of crystallizer used is not critical. The refrigeration can be supplied indirectly wherein the refrigeration does not mix with the process material. Typical examples include jackets surrounding the crystallization vessel or shell and tube heat exchanges external to the crystallization vessel. Propylene is a preferred refrigerant. Alternatively, the refrigeration can be supplied directly wherein the refrigeration, by design, is mixed with the process material. Typical examples include the injection of cold carbon dioxide or cold nitrogen into a draft tube crystallizer. Typical residence times in the crystallizers are in the range of about 30 minutes to about 5 hours, preferably about 30 minutes to about 3 hours, more preferably about 0.5 to about 2 hours.

Although not shown in FIG. 1, an alternate embodiment of the process in which either or both of two types of recycle streams are incorporated into the crystallization designs could be used to improve operability. The first recycle stream would recycle a portion of the crystallizer effluent back to the crystallizer 100. This could be represented in FIG. 1 by sending a portion of the slurry effluent in line 2 back to crystallizer 100. The second recycle stream would recycle a portion of one or more of the filtrate streams from the liquid-solid separation unit 30 immediately downstream of the crystallizer 100. This could be represented in FIG. 1 by sending at least a portion of the filtrate effluent in line 3 and/or line 4 back to crystallizer 100.

As shown in FIG. 1, an effluent stream from crystallizer 100 comprising a slurry of paraxylene crystals and mother liquor is conveyed through line 2 to a separation unit 30 comprising one or more liquid/solid separation devices. In a preferred embodiment, the liquid/solid separator 30 comprises one or more centrifuges which are used to separate paraxylene crystals from the mother liquor. Centrifuges used as separators in the process of the invention can be scraped bowl centrifuges or pusher centrifuges or a combination thereof. Other liquid/solid separation devices such as wash columns or rotary filters could also be used for separating paraxylene crystals in the process. Wash columns which could be used are, for example, NIRO wash columns or TNO hydraulic wash columns such as those described in U.S. Pat. Nos. 4,734,102 and 4,735,781 incorporated herein by reference in their entireties.

When all of the liquid/solid separators are centrifuges, it is preferable to use an initial feed containing a higher concentration of paraxylene, for example, at least about 80 wt % paraxylene, preferably at least about 85 wt % paraxylene, more preferably at least about 90 wt % paraxylene. When the temperature of the crystalline paraxylene slurry to be separated is below about 37° F., it is preferable to use wash columns to do the separation or, if using centrifuges, to wash with a solvent such as toluene. However, using toluene or another solvent rather than high purity paraxylene as the wash liquid will require an additional distillation step and additional equipment to separate the toluene from the paraxylene product which may increase the cost of the process.

When the liquid-solid separation device 30 is a centrifuge, it yields a product stream of washed paraxylene crystals. This paraxylene product stream is sent to a melt drum 35 via line 5 where the paraxylene crystals are completely melted to provide a high purity liquid paraxylene product. A portion of this high purity paraxylene is removed from melt drum 35 as product through product collection line 16 without further processing, i.e., without going through an additional cycle of crystallization and centrifugation. Taking a portion of the paraxylene from the first separation device directly to liquid paraxylene product without additional processing makes the process of the invention more efficient and more cost effective than crystallization processes which require further processing of the paraxylene crystals, such as recrystallization and recentrifugation. A washing operation may be performed in the separation device 30 to increase the purity of the paraxylene product stream 5 to 99.5 wt % paraxylene or higher, preferably 99.8 wt % paraxylene or higher. If a washing operation is performed, a portion of the paraxylene melt is returned to the separator 30 and sprayed on the paraxylene cake at the end of the separator 30. The ratio of wash liquid to crystalline paraxylene is suitably about 0.05 to about 0.5 by weight, preferably about 0.15 to about 0.25 by weight. When the liquid/solid separator is a centrifuge and purified paraxylene is used as a wash liquid, it is preferable that the temperature of the slurry of paraxylene crystals and mother liquor being separated be at a temperature of at least about 37° F. The liquid-solid separation device 30 also yields one or more filtrate streams conveyed via lines 3 (stream 3) and 4 (stream 4) in FIG. 1. Stream 3 is a reject filtrate stream, and stream 4 is a wash filtrate stream which contains more paraxylene than stream 3. For an embodiment in which stream 1 contains about 90 wt % paraxylene, stream 3 may contain about 81 wt % paraxylene and stream 4 may contain about 84 wt % paraxylene. These weight percentages may vary depending upon the type of centrifuge used and the wash ratio chosen. If the paraxylene product stream 5 contains solids, as is the case when centrifuges are used as the separation device, the solids can be melted to produce a liquid product. If a wash liquid is used, it can be either the liquid paraxylene product itself or other materials such as toluene or methanol. If the wash liquid is not the paraxylene product, then further separations are used to obtain the final purified paraxylene product and to recover the washing material(s). Two distillation columns are typically employed for this purpose. Preferably, the washing liquid will be a fraction of the paraxylene product.

For an embodiment wherein there is only one filtrate stream effluent from the separation device 30, line 4 in FIG. 1 has no effluent flow and can be eliminated. For a pusher centrifuge in product stage service, there are typically two filtrate streams as shown in FIG. 1. The composition of the filtrate in line 3 (stream 3, which is the reject filtrate, is lower in paraxylene than that of the filtrate in line 4 (stream 4), which is the wash filtrate. The filtrate in line 4 can be sent to a reslurry drum 32 via line 19 as a diluent as shown in FIG. 1. In order to control the temperature in reslurry drum 32, the filtrate stream conveyed via line 4 can be heated with the use of a heat exchanger (not shown) before being added to the reslurry drum.

A portion of the reject filtrate stream conveyed via line 3 can be sent to reslurry drum 32 via line 17 as diluent. The portion of stream 3 filtrate conveyed to reslurry drum 32 via line 17 can be heated, if desired, in order to control the temperature in the reslurry drum. The remaining portion of filtrate stream 3 may be combined with any filtrate from liquid-solid separator 31 in line 13 that is not recycled via line 18 to reslurry drum 32 to be used as diluent in reslurry drum 32. The combined streams from lines 3 and 13 are fed via line 25 to a second crystallizer 200 that operates at a lower temperature than the first crystallizer 100. Crystallizer 200 is operated at a temperature of from about −10° F. to about 35° F., preferably from about 15° F. to about 25° F. The effluent from the lower temperature crystallizer 200, which comprises crystalline paraxylene and mother liquor, is conveyed via line 6 to a separator 33 which comprises one or more liquid-solid separation devices. For the example shown, the effluent in line 6 is at about 25° F. The embodiment illustrated in FIG. 1 utilizes a single centrifuge as the separator 33 although more than one centrifuge or other separation means can be used. The crystalline paraxylene cake from centrifuge 33 is conveyed via line 8 to reslurry drum 32. The filtrate from centrifuge 33 is sent via line 7 to a third crystallizer 300 which is at a lower temperature than crystallizer 200. For an embodiment in which stream 1 contains about 90 wt % paraxylene, stream 7 will contain about 68 wt % paraxylene. Crystallizer 300 is operated at about −35° F. to about 5° F., preferably from about −10° F. to about −5° F. As explained above, other separation devices could be used in place of centrifuges 33 and 34. Although not shown in FIG. 1, one or more washing steps can be included, if desired. If washing is used, then multiple filtrate streams may be obtained, each with a different paraxylene composition. These filtrate streams can be either recycled back or fed forward to different parts of the design depending on their particular composition. The preferred embodiment does not use wash.

The effluent from crystallizer 300, which is a slurry comprising crystalline paraxylene and mother liquor, is fed via line 9 to a separator 34, which comprises one or more liquid-solid separation devices. In the embodiment illustrated in FIG. 1, the crystallizer effluent conveyed via line 9 is at about −5° F. In the embodiment illustrated, a single pusher centrifuge is used as the separator 34. The paraxylene cake from centrifuge 34 is sent via line 11 to the reslurry drum 32 while the filtrate is removed via line 10. The filtrate stream in line 10 can be used to cool the $C_8$ aromatic feed stream 1 before stream 1 enters the high temperature crystallizer 100. This will reduce the refrigeration requirement for this crystallizer. The filtrate stream in line 10 can then be sent to either a reactor, such as a reactor that converts ethylbenzene to other compounds that can be separated more easily from the other $C_8$ aromatics, or to another separation process. For an embodiment in which stream 9 is at −5° F., stream 10 will contain about 45 wt % paraxylene.

The reslurry drum 32 is operated at a sufficiently high temperature so that the effluent from the reslurry drum can be sent to one or more liquid-solid separation devices that are capable of producing more high purity product. Although not necessary, the temperature of the reslurry drum may be higher than that of any of the aforementioned crystallizers. In all cases, it will be warmer than the lowest temperature crystallizer. The temperature of the slurry is suitably at least about 10° F., preferably about 30° F., more preferably about 35° F. to about 45° F., more preferably at a temperature of about 38° F. to about 42° F., and most preferably at a temperature of about 40° F. to about 42° F. Crystalline paraxylene is contacted with paraxylene-containing liquid in a slurry for a time sufficient to allow the crystals and the mother liquor to approach equilibrium. This time is preferably about 0.1 to about 2 hours, more preferably about 0.4 to about 1 hour. The amount of liquid in the slurry should be an amount sufficient to produce a mixture that can be slurried and pumped. The liquid used for the slurry is a liquid which contains paraxylene. Those streams having higher concentrations are more preferred for use as slurry liquid. For example, for the embodiment shown in FIG. 1, streams 4 and 14 would preferably be chosen first, and then stream 3 and/or stream 13. After the slurry is sufficiently equilibrated, the purified crystalline paraxylene is separated from the liquid and preferably washed with liquid paraxylene to remove adhering mother liquor. The liquid paraxylene used for the wash is preferably high purity paraxylene having a purity of at least about 99.5 weight percent, preferably at least about 99.7 weight percent, more preferably at least about 99.8 weight percent. The weight ratio of liquid paraxylene wash to crystalline paraxylene is typically about 0.05:1 to about 0.5:1, more preferably about 0.15:1 to about 0.25:1; still more preferably about 0.18:1 to about 0.2:1. Upon melting the purified crystalline paraxylene, a liquid product paraxylene having a purity of at least 99.5 weight percent, more preferably at least about 99.7 weight percent, and most preferably at least about 99.8 weight percent is produced.

In cases where the reslurry drum 32 is warmer than crystallizer 100, it is possible that the concentration of paraxylene in the filtrate stream in line 13 can approach or exceed the concentration of the paraxylene feed in line 1. In such cases, the fraction of the filtrate stream in line 13 that is not recycled to the reslurry drum 32 can be sent to crystallizer 100 rather than to crystallizer 200, further improving the energy efficiency of the process. This is the process shown in FIG. 2. Reslurry drum 32 is operated at about 10° F. to about 55° F., preferably from about 30° F. to about 50° F.

A slurry of paraxylene crystals and paraxylene-containing liquid is prepared in reslurry drum 32. The paraxylene-containing liquid used to prepare the slurry of crystalline paraxylene and liquid paraxylene can be one or more of the mother liquor streams produced by separating the crystalline paraxylene from liquid mother liquor. The paraxylene-containing liquid used for the slurry is an amount suitable for providing for the slurry of crystalline paraxylene and liquid. For an embodiment in which stream 1 in FIG. 1 contains about 90 wt % paraxylene, the liquid to the reslurry drum preferably comprises all of stream 4, which is 84 wt % paraxylene, all of stream 14, which is 86 wt % paraxylene, and 32% of stream 13, which is 83 wt % paraxylene. Typically, the remainder is a mixture of ortho- and meta-xylene, ethylbenzene and other hydrocarbons from the process. The amount of crystalline paraxylene in the slurry is typically about 30 to about 60 weight percent, preferably about 30 to about 55 weight percent, and most preferably about 35 to about 50 weight percent. This slurry is preferably agitated, preferably by a mechanical agitator. The slurry is retained in the slurry vessel 32 for a time sufficient to permit all of the slurry to approach equilibrium. For the preferred continuous operation of this embodiment of the invention, the residence time for this slurry in the slurry vessel 32 is suitably about 0.2 to about 2 hours, more preferably about 0.4 to about 1 hour.

The liquid-solids separator 31 is fed from the reslurry drum 32. The types of separation devices that can be used have already been discussed in connection with stream 2 above. In one embodiment of the process illustrated in FIG. 1, two centrifuges are used. Washing (not shown) may also be provided. When washing is used, a portion of the purified paraxylene melt from melt drum 35 is used to wash the paraxylene cake at the end of the centrifuge. The crystalline paraxylene cake from separator 31 is sent to melt drum 35 via line 15 and the paraxylene crystals are completely melted to provide purified paraxylene product. A portion of the paraxylene melt may be recycled to centrifuge 31 as a wash liquid. For the embodiment shown in FIG. 1, the paraxylene stream in line 15 is a paraxylene product stream from centrifuge 31, and the filtrate streams in lines 13 and 14 are the filtrate streams from centrifuge 31. The total paraxylene product stream is conveyed from the melt drum 35 via line 16 and is the combination of the paraxylene product streams from lines 5 and 15. The filtrate stream in line 14 (the wash filtrate) has a higher composition of paraxylene than the filtrate stream in line 13 (the reject filtrate). The wash filtrate stream in line 14 can be combined with the wash filtrate stream in line 4 and sent via line 19 to the reslurry drum 32 as diluent. A portion of the reject filtrate stream in line 13 can also be sent to the reslurry drum 32 as diluent. The remaining portion of reject filtrate stream 13 is combined with reject filtrate stream 3 and sent to crystallizer 200, as discussed above. Any or all of the streams used as diluent in the reslurry drum can be warmed through the use of a heat exchanger (not shown). Moreover, some or all the various diluent streams can be combined before entering the reslurry drum or before passing through a heat exchanger. Other alternatives for controlling the reslurry drum temperature, such as warming the reslurry drum through the use of a steam jacket, may also be used.

There are two important concepts in the invention. The first concept centers on the first stage of crystallization and separation. By the appropriate choice of process conditions and equipment, the first stage is capable of producing high purity product (stream 5) that does not require further processing.

In the example provided, over 50% of the final product (the stream in line 16 which is a combination of product streams 5 and 15), which has a purity of about 99.85 wt % paraxylene, is obtained from the first crystallization/separation stage. This material does not go through the downstream equipment; therefore, the energy requirements are reduced and probably the capital costs are also reduced compared with most other processes (particularly those discussed in U.S. Pat. No. 6,111,161).

The second important concept centers on the reslurry drum, whose function is to warm all the cake that is too cold to conveniently yield high purity paraxylene product directly. Most importantly, the reslurry drum requires no refrigeration, which reduces energy costs compared with other process designs, although it may require heat. Therefore, the cake from the colder crystallization stages can be processed using the reslurry drum to yield high purity paraxylene product (the crystalline paraxylene stream in line 15) without the need for further refrigeration. (The use of this reslurry drum makes the present invention significantly different from the invention disclosed in U.S. Pat. No. 5,448,005.) Finally, the reslurry drum in the present invention is not simply a device to partially melt crystals to make a suspension. The reslurry drum in this invention is capable, as in the example provided above, of yielding more crystalline paraxylene solids in the slurry drum effluent than provided in all the various input streams, despite the addition of heat. Therefore, the present invention also includes those embodiments wherein the amount of paraxylene crystals in the slurry mixture formed in the slurry apparatus is greater than the amount of paraxylene crystals sent to the slurry apparatus.

The temperatures of the various crystallization stages and the number of the crystallization stages will vary depending on the refrigeration cycle(s) chosen, the refrigerant(s) chosen, and the composition of stream 1. The choice of separation equipment may also alter the schematic and the ultimate purity of the paraxylene product. For example, wash columns typically have only one reject filtrate stream and they may yield a higher purity product than centrifuges.

Figure 2:
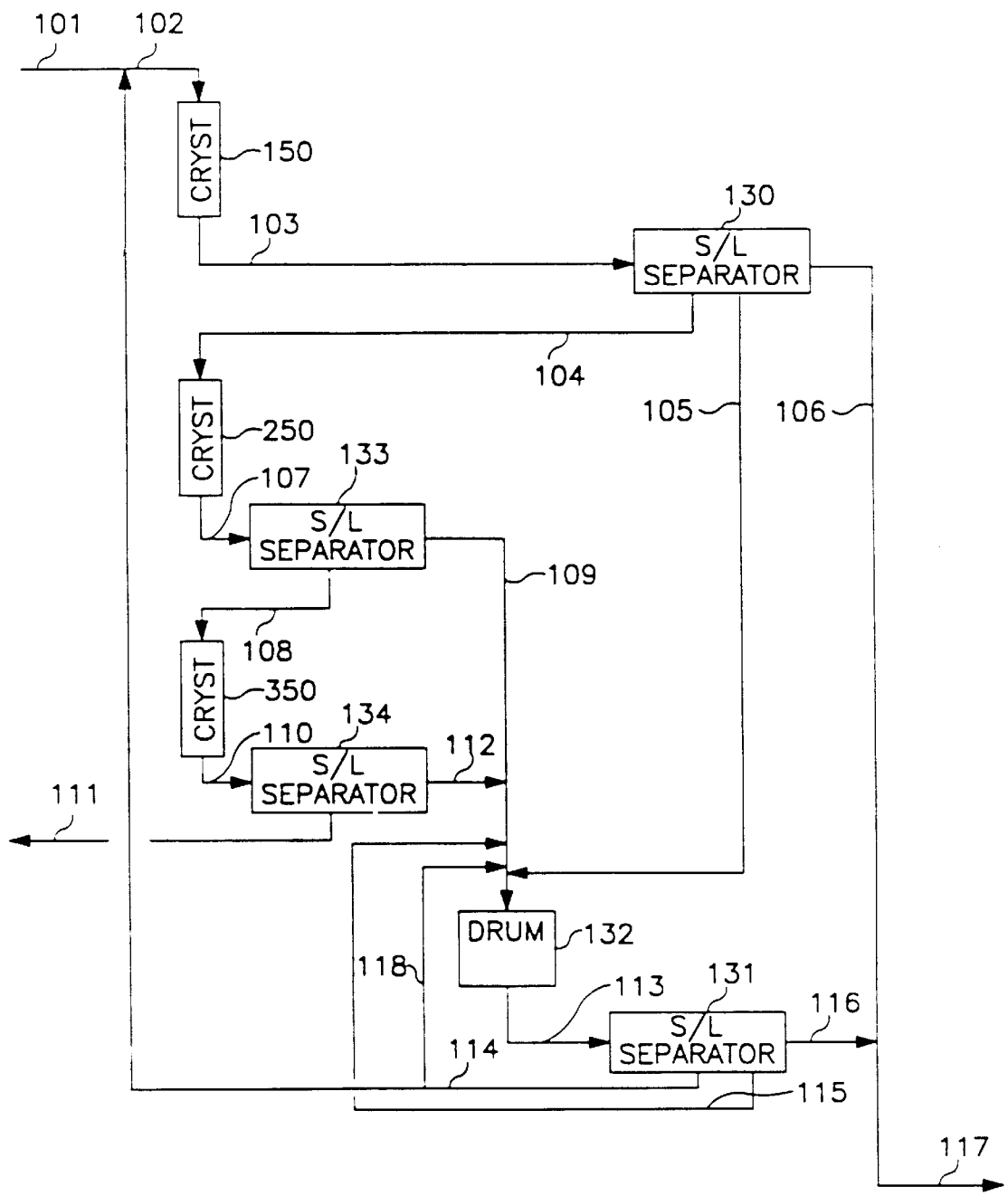
FIG. 2 shows a schematic of an embodiment of the present invention in which at least a portion of the reject filtrate from the separation of the effluent from the reslurry drum is combined with the feed going to the first crystallization step rather than being sent to the second crystallization step.

Another embodiment of the process of the present invention is illustrated in FIG. 2. A feed (stream 102) comprising at least about 55 wt % paraxylene is sent via line 102 to crystallizer 150. It is desirable that the composition of stream 102 be at least about 55 weight percent (wt %) paraxylene, preferably greater than about 55 wt % paraxylene, more preferably at least about 60 wt % paraxylene, more preferably at least about 70 wt % paraxylene, more preferably at least about 75 wt % paraxylene, more preferably at least about 80 wt % paraxylene, more preferably at least about 85 wt % paraxylene, more preferably at least about 90 wt % paraxylene, and most preferably at least about 95 wt % paraxylene. Crystallizer 150 is operated at a temperature of about 10° F. to about 55° F., preferably about 20° F. to about 30° F.

The crystallizer 150 effluent, which comprises paraxylene crystals and mother liquor, is sent to a separation unit 130 comprising one or more centrifuges which are used to separate paraxylene crystals from the mother liquor. Separation devices other than centrifuges, such as wash columns or rotary filters, can also be used in this step and in other steps in the process where liquid-solids separation devices are used. The crystalline paraxylene cake is washed inside the centrifuges using high purity paraxylene material. The centrifuges 130 produce high purity paraxylene product (stream 106) and two filtrate streams (streams 104 and 105). Stream 105 is the wash filtrate and is more concentrated in paraxylene than the reject filtrate, stream 104. All of the wash filtrate is sent to the reslurry drum 132 to provide some of the liquid for the reslurry operation. All of the reject filtrate is sent via line 104 to crystallizer 250, which operates at a temperature lower than that of crystallizer 150. Crystallizer 250 is operated at a temperature of from about −10° F. to about 35° F., preferably from about 5° F. to about 15° F.

The effluent from crystallizer 250, which comprises a slurry of crystalline paraxylene in mother liquor, is sent via line 107 to separation unit 133, which comprises at least one centrifuge or other separation means. The crystalline paraxylene cake from the centrifuge 133 is conveyed via line 109 into the reslurry drum 132 while the reject filtrate (stream 108) is sent via line 108 to crystallizer 350, which operates at a temperature lower than crystallizer 250. Crystallizer 350 is operated at a temperature of from about −35° F. to about 5° F., preferably from about −10° F. to about −5° F.

The effluent from crystallizer 350 (stream 110) which comprises a slurry of crystalline paraxylene in mother liquor is sent via line 110 to separation unit 134 which comprises at least one centrifuge or other separation means. The crystalline paraxylene cake from the centrifuge is dropped into reslurry drum 132. The reject filtrate (stream 111) contains about 45 wt % paraxylene and is heat exchanged with feed stream 101 before being sent elsewhere in the unit. For example, it may be sent to an ethylbenzene reactor or to another separation process. The slurry from reslurry drum 132, which comprises crystalline paraxylene and mother liquor, is sent via line 113 to a separation unit 131 comprising one or more centrifuges where the crystalline paraxylene is separated from the mother liquor. The crystalline paraxylene cake is washed inside these centrifuges using high purity paraxylene material. These centrifuges produce additional high purity paraxylene product, stream 116, which is combined with high purity paraxylene product stream 106, melted in a melt drum (not shown) if necessary, and collected via line 117. Separation unit 131 also produces two filtrate streams (streams 114 and 115). Stream 115 is the wash filtrate and is more concentrated in paraxylene than the reject filtrate, stream 114. All of the wash filtrate is sent via line 115 to the reslurry drum 132 to provide some of the liquid for the reslurry operation. A portion of the reject filtrate is sent via line 114 to the reslurry drum 132 to provide the rest of the liquid for the reslurry operation. The reslurry drum 132 is operated at a temperature of from about 10° F. to about 55° F., preferably from about 30° F. to about 50° F., more preferably from about 35° F. to about 45° F., more preferably from about 38° F. to about 42° F., and most preferably at a temperature from about 40° F. to about 42° F. The remaining reject filtrate (stream 114) from separation unit 131 is combined with stream 101 upstream of crystallizer 150 to form feed stream 102. For an embodiment in which stream 102 contains about 70 wt % paraxylene, stream 114 will contain about 83 wt % paraxylene. In this embodiment of the process of the invention, crystallizer 150 is operated at a temperature of from about 10° F. to about 55° F., preferably from about 20° F. to about 30° F. Crystallizer 250 is operated at a temperature of from about −10° F. to about 35° F., preferably from about 5° F. to about 15° F., and crystallizer 350 is operated at a temperature of from about −35° F. to about 5° F., preferably from about −10° F. to about −5° F.

The following examples will serve to illustrate certain embodiments of the invention disclosed herein. These examples should not, however, be construed as limiting the scope of the novel invention as there are many variations which may be made thereon without departing from the spirit of the disclosed invention, as those of skill in the art will recognize.

Calculations of performance in the examples are made according to standard engineering practices. For a particular comparison, the feed and the product were identical between each comparable example. Each example had three refrigeration levels available. The effluent from the coldest crystallizer was set at −5° F. in each case, ensuring that the overall paraxylene recovery for each comparable example was nearly identical. The temperature for the other two crystallization stages was chosen to shift as much duty to the warmest crystallizer while still maintaining a reasonable balance between the stages. Overriding this criterion was the need to keep the first stage of crystallizers warm enough to allow for the production of high purity product from the first set of separation devices for the designs based on FIG. 1 and FIG. 2. One would expect that keeping the first stage crystallizers at a warmer temperature would shift more refrigeration duty to the lower temperature crystallizers (which it did). One would also expect that this would increase the refrigeration compressor power requirements relative to the comparative example; however, this, unexpectedly, was not the case. The process designs of FIG. 1 and FIG. 2 required less compressor power, and this was surprising and non-obvious. This shows that the process of the present invention has the advantage of being more energy efficient, and, therefore, will also be expected to be less costly.

Example 1, Example 2, and Comparison Example A compare the performance of three different processes all producing 115,840 lb/hr of paraxylene product having a purity of 99.80 wt % paraxylene. Examples 1 and 2 illustrate embodiments of the present invention in which a portion of the total high purity paraxylene product is made from the effluent from the first crystallization without subjecting it to a reslurry step or a partial melting step, and Comparison Example A illustrates a comparison process in which the crystalline paraxylene cake from the first crystallization/separation does not go to product, but instead is combined with the crystalline paraxylene cakes from subsequent lower temperature crystallization/separation steps and subjected to a reslurry step.

For each process, a feed containing 90 wt % paraxylene is used, and the high purity paraxylene product contains 99.8 wt % paraxylene. The overall paraxylene recovery for each example is 91%. Centrifuges are used for all liquid/solid separations. When Example 1, Example 2, and Comparison Example A are compared, the process of Example 1 is the most energy efficient and the process of Example 2 is the next most energy efficient. The process design of Example 2, illustrated by FIG. 2, requires about 3% more refrigeration compressor power for the same production rate of 115,840 lb/hr of paraxylene product having a purity of 99.80 wt % paraxylene than the process of Example 1, whereas the process of Comparison Example A requires about 5% more refrigeration compressor power than the process of Example 1.

EXAMPLE 1

For this example, the operation of an embodiment of the process illustrated in the flow scheme of FIG. 1 is shown to be the most energy efficient of the three process designs (Example 1, Example 2, and Comparison Example A) based on the power consumption of the propylene refrigeration compressor. A feed containing 90% paraxylene is cooled in crystallizer 100 to a temperature of 40.5° F. The crystallizer effluent is sent to a separation unit 30 comprising two centrifuges. The crystalline paraxylene cake is washed inside the centrifuges using high purity paraxylene material. The centrifuges produce 63,120 lb/hr of high purity product, stream 5, and two filtrate streams (streams 3 and 4). Stream 4 is the wash filtrate, and it has a greater paraxylene concentration than the reject filtrate, stream 3. All of the wash filtrate (stream 4) is sent to the reslurry drum 32 to provide some of the liquid necessary for the reslurry operation. All of the reject filtrate (stream 3) is sent to crystallizer 200. Crystallizer 200 is operated at 25° F. The effluent from crystallizer 200 is sent to a separation unit 33 comprising a centrifuge. The crystalline paraxylene cake from the centrifuge is dropped into the reslurry drum 32, while the reject filtrate is sent via line 7 to crystallizer 300, which operates at −5° F. The effluent from this crystallizer is also sent to a separation unit 34 comprising a centrifuge. The crystalline paraxylene cake from centrifuge 34 is dropped into reslurry drum 32. The reject filtrate stream in line 10 contains about 45 wt % paraxylene and is heat exchanged with the feed, stream 1, before being sent elsewhere in the unit. The slurry from reslurry drum 32 is sent to separation unit 31 comprising two centrifuges. The crystalline paraxylene cake is washed inside these centrifuges using high purity paraxylene material. These centrifuges produce an additional 52,720 lb/hr of high purity paraxylene product (stream 15), which is combined with the high purity paraxylene product in line 5 (stream 5), melted, and collected via line 16. Stream 14 is the wash filtrate and is more concentrated in paraxylene than the reject filtrate, stream 13. All of the wash filtrate is sent via line 14 to the reslurry drum 32 to provide some of the liquid for the reslurry operation. About 32% of the reject filtrate is sent to the reslurry drum 32 to provide the rest of the liquid for the reslurry operation. The reslurry drum operates at 42° F. The remaining reject filtrate from separation unit 31 is combined with stream 3 upstream of crystallizer 200 and sent to crystallizer 200. Three levels of propylene refrigeration are used in this example at pressures of about 66, 48 and 26 psia. The refrigeration compressor requires about 2707 horsepower (hp).

EXAMPLE 2

The process design illustrated by FIG. 2 requires about 3% more refrigeration compressor power for the same production rate of 115,840 lb/hr of paraxylene product having a purity of 99.80 wt % paraxylene. A feed containing 90% paraxylene (stream 102) is sent to crystallizer 150 which operates at a temperature of 40° F. The crystallizer effluent is sent to a separation unit 130 comprising three centrifuges. The crystalline paraxylene cake is washed inside the centrifuges using high purity paraxylene material. The centrifuges 130 produce 69,100 lb/hr of high purity product (stream 106) and two filtrate streams (streams 104 and 105). Stream 105 is the wash filtrate and is more concentrated in paraxylene than the reject filtrate, stream 104. All of the wash filtrate is sent to the reslurry drum 132 to provide some of the liquid necessary for the reslurry operation. All of the reject filtrate is sent to crystallizer 250. Crystallizer 250 is operated at 25° F. The effluent is sent to separation unit 133 comprising one centrifuge. The crystalline paraxylene cake from the centrifuge 133 is dropped into the reslurry drum 132 while the reject filtrate (stream 108) is sent to crystallizer 350, which operates at −5° F. The effluent from this crystallizer (stream 110) is sent to separation unit 134 comprising one centrifuge. The crystalline paraxylene cake from the centrifuge is dropped into reslurry drum 132. The reject filtrate (stream 111) contains about 45 wt % paraxylene and is heat exchanged with feed stream 101 before being sent elsewhere in the unit. The slurry from reslurry drum 132, which comprises crystalline paraxylene and mother liquor, is sent via line 113 to a separation unit 131 comprising two centrifuges and separated. The crystalline paraxylene cake is washed inside these centrifuges using high purity paraxylene material. These centrifuges produce an additional 46,740 lb/hr of high purity product, stream 116 which is combined with product stream 106, melted, and collected via line 117. Separation unit 131 also produces two filtrate streams (streams 114 and 115). Stream 115 is the wash filtrate and is more concentrated in paraxylene than the reject filtrate, stream 114. All of the wash filtrate is sent to the reslurry drum 132 to provide some of the liquid necessary for the reslurry operation. About 6% of the reject filtrate is sent to the reslurry drum 132 to provide the rest of the liquid necessary for the reslurry operation. The reslurry drum operates at 42° F. The remaining reject filtrate (stream 114) from centrifuges 131 is combined with stream 101 upstream of crystallizer 150 to form feed stream 102. Three levels of propylene refrigeration are used in this example at pressures of about 63, 48 and 26 psia. The refrigeration compressor requires about 2791 hp, which is 3.1% higher than the horsepower required for the design depicted in FIG. 1 (Example 1).

COMPARISON EXAMPLE A

Figure 3:
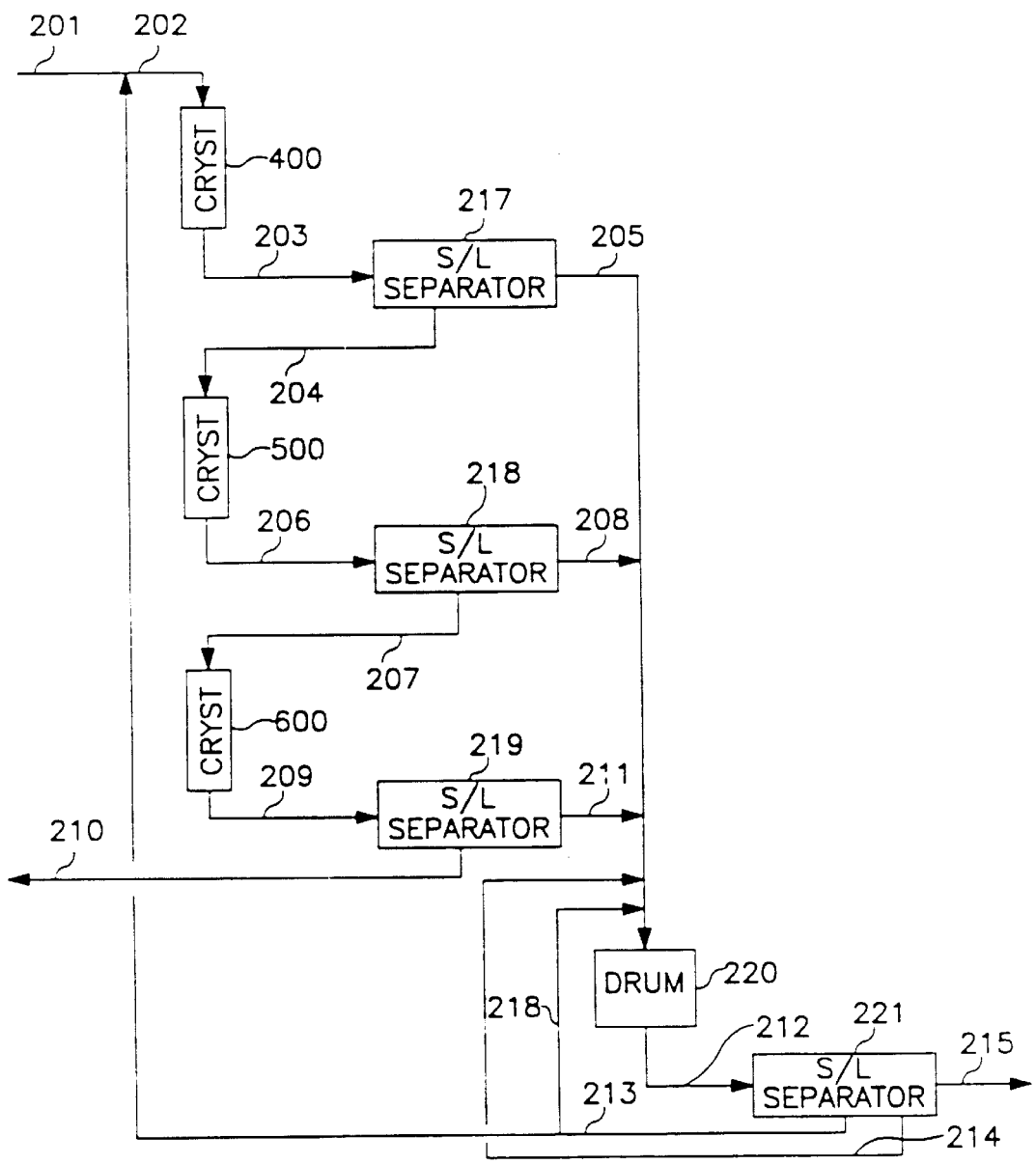
FIG. 3 shows a process in which the crystalline paraxylene formed in the first crystallization step does not go to paraxylene product following crystallization and separation but is combined with the crystalline paraxylene cakes formed in the second and third crystallization/separation steps and then subjected to a reslurry step.

A comparison process design in which the crystalline paraxylene cakes from the separation devices that process the effluents of all three crystallization steps are combined and subjected to a reslurry operation (illustrated in FIG. 3) requires about 5% more refrigeration compressor power than the process of Example 1 for the same production rate of 115,840 lb/hr of paraxylene product having a purity of 99.80 wt % paraxylene. A feed containing 90% paraxylene is sent to crystallizer 400 which operates at a temperature of 39.5° F. The crystallizer effluent is sent via line 203 to a separation unit 217 comprising two centrifuges. The crystalline paraxylene cake from these centrifuges is dropped via line 205 into the reslurry drum 220. The reject filtrate, stream 204, is sent to crystallizer 500 which operates at 25.5° F. The effluent from crystallizer 500 is sent via line 206 to separation unit 218 comprising one centrifuge. The crystalline paraxylene cake from separation unit 218 is dropped via line 208 into reslurry drum 220. The reject filtrate, stream 207, is sent to crystallizer 600 which operates at −5° F. The effluent from this crystallizer (stream 209) is sent to separation unit 219 comprising one centrifuge. The crystalline paraxylene cake from separation unit 219 is dropped via line 211 into reslurry drum 220. The reject filtrate (stream 210) contains about 45 wt % paraxylene and is heat exchanged with the feed, stream 201, before being sent elsewhere in the unit. The slurry from the reslurry drum 220 is sent via line 212 to a separation unit 221 comprising four centrifuges. The crystalline paraxylene cake is washed inside these centrifuges using high purity paraxylene material. These centrifuges produce the entire 115,840 lb/hr of high purity product, stream 215. Stream 214 is the wash filtrate and is more concentrated in paraxylene than the reject filtrate, stream 213. All of the wash filtrate is sent to the reslurry drum 220 to provide some of the liquid necessary for the reslurry operation. About 82% of the reject filtrate is sent to the reslurry drum 220 via line 218 to provide the rest of the liquid necessary for the reslurry operation. The reslurry drum operates at 42° F. The remaining reject filtrate from the centrifuges is combined with feed stream 201 upstream of crystallizer 400 to form feed stream 202. Three levels of propylene refrigeration are used in this example at pressures of about 63, 48 and 26 psia. The refrigeration compressor requires about 2837 hp, which is 4.8% higher than for the design depicted in FIG. 1.

Example 3, Example 4, and Comparison Example B compare the performance of three different processes all producing 115,840 lb/hr of paraxylene product having a purity of 99.90 wt % paraxylene. For each process, a feed containing 90 wt % paraxylene is used. The overall paraxylene recovery for each example is 91%. The processes described in Example 3, Example 4, and Comparison Example B are the same as the processes described in Example 1, Example 2, and Comparison Example A respectively with the exception that TNO hydraulic wash columns are used for some of the liquid/solids separations to produce the high purity paraxylene product rather than using centrifuges throughout as liquid/solids separators. Examples 3 and 4 illustrate embodiments of the present invention while Comparison Example B illustrates a comparison process. It can be seen that when Example 3, Example 4, and Comparison Example B are compared, the process of Example 3 is the most energy efficient, and the process of Example 4 is more energy efficient than the process of Comparison Example B. The process of Example 4 requires only about 2% more refrigeration compressor power than the process of Example 3 for the same production rate of 115,840 lb/hr of paraxylene product having a purity of 99.90 wt %, whereas the process of Comparison Example B requires about 7% more refrigeration compressor power than the process of Example 3.

EXAMPLE 3

In this example, the operation of an embodiment of the process of the invention illustrated in the flow scheme of FIG. 1 is shown. This embodiment of the process illustrated in the flow scheme of FIG. 1 is shown to be the most energy efficient of the three process designs (Examples 3, 4, and Comparison Example B) based on the power consumption of the propylene refrigeration compressor. A feed containing 90 wt % paraxylene is cooled in crystallizer 100 to a temperature of 40.5° F. The crystallizer effluent is sent to separation unit 30 comprising two TNO hydraulic wash columns (see U.S. Pat. Nos. 4,734,102 and 4,735,781, incorporated herein by reference in their entireties, for descriptions of these wash columns). The wash columns produce 66,410 lb/hr of high purity product, stream 5, and a single filtrate stream, stream 3. All of stream 3 is sent to crystallizer 200. Since wash columns are used, there is no stream 4 in this embodiment. Crystallizer 200 is operated at 25° F. The effluent from crystallizer 200 is sent to a separation unit 33 comprising one centrifuge. The cake from the centrifuge 33 is dropped into reslurry drum 32, while the reject filtrate (stream 7) is sent to crystallizer 300, which operates at −5° F. The effluent from this crystallizer is also sent to a separation unit 34 comprising one centrifuge. The cake from centrifuge 34 is dropped into reslurry drum 32. The reject filtrate (stream 10) contains about 45 wt % paraxylene and is heat exchanged with the feed stream 1 before being sent elsewhere in the unit. The slurry from reslurry drum 32 is sent to separation unit 31 comprising one TNO hydraulic wash column. This wash column produces an additional 49,430 lb/hr of high purity product (stream 15). About 84% of the filtrate from the wash column is sent to the reslurry drum 32 to provide the liquid for the reslurry operation. The reslurry drum operates at 42° F. The remaining filtrate from the wash column is combined with stream 3 upstream of crystallizer 200. In this example, stream 14 does not exist. Three levels of propylene refrigeration are used in this example at pressures of about 66, 48 and 26 psia. The refrigeration compressor requires about 2670 hp.

EXAMPLE 4

In this example, the operation of an embodiment of the process illustrated in the flow scheme of FIG. 2 is shown. This embodiment of the process requires about 2% more refrigeration compressor power for the same production rate of 115,840 lb/hr of paraxylene product having a purity of 99.90 wt % paraxylene. A feed containing 90 wt % paraxylene is sent via line 102 to crystallizer 150 which operates at a temperature of 40° F. The crystallizer effluent is sent to separation unit 130 comprising three TNO hydraulic wash columns. The wash columns produce 70,040 lb/hr of high purity product, stream 106, and a single filtrate stream, stream 104, which is sent to crystallizer 250. There is no stream 105 for this particular example. Crystallizer 250 is operated at 24° F. The effluent from crystallizer 250 is sent to separation unit 133 comprising one centrifuge, and paraxylene crystals are separated from the mother liquor. The crystalline paraxylene cake from the centrifuge 133 is dropped into the reslurry drum 132 while the reject filtrate (stream 108) is sent to crystallizer 350, which operates at −5° F. The effluent from crystallizer 350 is sent to separation unit 134 comprising one centrifuge, and paraxylene crystals are separated from the mother liquor. The crystalline paraxylene cake from the centrifuge is dropped into reslurry drum 132. The reject filtrate (stream 111) contains about 45 wt % paraxylene and is heat exchanged with the feed, stream 101, before being sent elsewhere in the unit. The slurry from reslurry drum 132 is sent to separation unit 131 comprising two TNO hydraulic wash columns. These wash columns produce an additional 45,800 lb/hr of high purity paraxylene product (stream 116) which is combined with high purity paraxylene product stream 106 and collected via line 117. About 84% of the filtrate (stream 114) from separation unit 131 is sent to the reslurry drum 132 via line 118 to provide liquid for the reslurry operation. The reslurry drum operates at 42° F. The remaining filtrate from the wash column combines via line 114 with feed stream 101 upstream of crystallizer 150. In this example, stream 115 does not exist. Three levels of propylene refrigeration are used in this example at pressures of about 63, 47 and 26 psia. The refrigeration compressor requires about 2718 hp, which is 1.8% higher than for the design depicted in FIG. 1.

COMPARISON EXAMPLE B

A comparison process design, in which the crystalline paraxylene cakes from the separation devices that process the effluents of all three crystallization steps are combined and subjected to a reslurry operation (illustrated in FIG. 3), requires about 7% more refrigeration compressor power than the design for the process of the present invention shown in Example 3 above for the same production rate of 115,840 lb/hr of paraxylene product having a purity of 99.90 wt % paraxylene. A feed containing 90 wt % paraxylene (stream 202) is sent to crystallizer 400, which operates at a temperature of 39° F. The crystallizer effluent is sent to separation unit 217 comprising two centrifuges, and paraxylene crystals are separated from the mother liquor. The crystalline paraxylene cake from these centrifuges is dropped into the reslurry drum 220 via line 205. The reject filtrate, stream 204, is sent to crystallizer 500 which operates at 25° F. The effluent is sent via line 206 to separation unit 218 comprising one centrifuge. The crystalline paraxylene cake from separation unit 218 is dropped via line 208 into reslurry drum 220. The reject filtrate (stream 207) is sent to crystallizer 600 which operates at −5° F. The effluent from this crystallizer is sent via line 209 to separation unit 219 comprising one centrifuge. The crystalline paraxylene cake from separation unit 219 is dropped via line 211 into reslurry drum 220. The reject filtrate (stream 210) contains about 45 wt % paraxylene and is heat exchanged with feed stream 201, before being sent elsewhere in the unit. The slurry from the reslurry drum 220 is sent via line 212 to separation unit 221 comprising three TNO hydraulic wash columns. These wash columns produce the entire 115,840 lb/hr of high purity paraxylene product, which is collected via line 215. About 90% of the filtrate from the wash columns (stream 213) is sent via line 218 to reslurry drum 220 to provide the liquid necessary for the reslurry operation. The reslurry drum operates at 42° F. The remaining filtrate from the wash columns is combined with stream 201 upstream of crystallizer 400 to form feed stream 202. In this example, stream 214 does not exist. Three levels of propylene refrigeration are used in this example at pressures of about 62, 48 and 26 psia. The refrigeration compressor requires about 2849 hp, which is 6.7% higher than for the process design of Example 4.

Example 5, Example 6, and Comparison Example C compare the performances of three different processes all producing 115,840 lb/hr of paraxylene product having a purity of 99.90 wt % paraxylene. The processes described in Example 5, Example 6, and Comparison Example C are the same as the processes described in Example 3, Example 4, and Comparison Example B, respectively, with the exception that the concentration of paraxylene in the initial feed is lower. For each process, a feed containing 70 wt % paraxylene is used. The overall paraxylene recovery for each example is 69%. Examples 5 and 6 illustrate embodiments of the present invention while Comparison Example C illustrates a comparison process. It can be seen that when Example 5, Example 6, and Comparison Example C are compared, the process of Example 6 is the most energy efficient and the process of Example 5 is the next most energy efficient. For the process embodiment of Example 5, the refrigeration compressor requires about 4884 hp, which is 8.9% greater than that needed for the process of Example 6. For the process of Comparison Example C, the refrigeration compressor requires about 5178 hp, which is 15.5% higher than the horsepower required for the process of Example 6 and 6.0% higher than the horsepower required for the process of Example 5.

EXAMPLE 5

In this example of an embodiment of the invention, the process embodiment illustrated by the flow scheme of FIG. 1 is shown to require about 9% more refrigeration compressor power than the process embodiment design depicted in FIG. 2. A feed containing 70 wt % paraxylene is cooled in crystallizer 100 to a temperature of 22° F. The crystallizer effluent, which comprises paraxylene crystals and mother liquor, is sent to separation unit 30 comprising four TNO hydraulic wash columns. The wash columns produce 51,940 lb/hr of high purity product (stream 5) and a single filtrate stream (stream 3). In this embodiment, all of stream 3 is sent via line 3 to crystallizer 200. Since wash columns are used, there is no stream 4 for this particular example. Crystallizer 200 is operated at 14° F. The effluent is sent via line 6 to separation unit 33 comprising three centrifuges where the crystalline paraxylene is separated from the mother liquor. The crystalline paraxylene cake from the centrifuges is dropped into the reslurry drum 32, while the reject filtrate is sent via line 7 to crystallizer 300, which operates at −5° F. The effluent from crystallizer 300, which comprises crystalline paraxylene and mother liquor, is sent to separation unit 34 comprising two centrifuges for separation. The crystalline paraxylene cake from the centrifuges is dropped into reslurry drum 32. The reject filtrate (stream 10) contains about 42 wt % paraxylene and is heat exchanged with the feed (stream 1) before being sent elsewhere in the unit. The slurry from reslurry drum 32 is sent to separation unit 31 comprising two TNO hydraulic wash columns. These wash columns produce an additional 63,900 lb/hr of high purity paraxylene product, stream 15, which is combined with high purity paraxylene product stream 5 and collected in line 16. About 29% of the filtrate from the wash column 31 is sent to the reslurry drum 32 to provide liquid for the reslurry operation. The reslurry drum operates at 42° F. The remaining filtrate from the wash column 31 is combined with stream 3 upstream of crystallizer 200. In this example, stream 14 does not exist. Three levels of propylene refrigeration are used in this example at pressures of about 47, 39 and 26 psia. The refrigeration compressor requires about 4884 hp, which is 8.9% greater than that needed for the design depicted in Example 6 (FIG. 2).

EXAMPLE 6

In this example of an embodiment of the invention, the process embodiment illustrated by the flow scheme of FIG. 2 is shown to be the least energy intensive of the three designs (Example 5, Example 6, and Comparison Example C) based on the power consumption of the propylene refrigeration compressor for this example. A feed containing 70 wt % paraxylene is sent to crystallizer 150 which operates at a temperature of 24° F. The crystallizer effluent, which comprises crystalline paraxylene and mother liquor, is sent to separation unit 130 comprising three TNO hydraulic wash columns. The wash columns produce 68,350 lb/hr of high purity product (stream 106) and a single filtrate stream (stream 104) which is sent via line 104 to crystallizer 250. There is no stream 105 for this particular example. Crystallizer 250 is operated at 11° F. The effluent from crystallizer 250 is sent to separation unit 133 comprising three centrifuges. The crystalline paraxylene cake from the centrifuges is dropped into the reslurry drum 132, while the reject filtrate is sent via line 108 to crystallizer 350, which operates at −5° F. The effluent from this crystallizer is sent to separation unit 134 comprising two centrifuges. The crystalline paraxylene cake from the centrifuges is dropped into reslurry drum 132. The reject filtrate (stream 111) contains about 42 wt % paraxylene and is heat exchanged with the feed (stream 101) before being sent elsewhere in the unit. The slurry from reslurry drum 132 is sent to separation unit 131 comprising a TNO hydraulic wash column. This wash column produces an additional 47,490 lb/hr of high purity paraxylene product, stream 116, which is combined with high purity paraxylene product stream 106 and collected via line 117. About 34% of the filtrate from the wash column (stream 114) is sent to the reslurry drum 132 to provide liquid for the reslurry operation. The reslurry drum operates at 42° F. The remaining filtrate from the wash column 131 is combined with stream 101 upstream of crystallizer 150 to form stream 102. In this example, stream 115 does not exist. Three levels of propylene refrigeration are used in this example at pressures of about 47, 36 and 26 psia. The refrigeration compressor requires about 4483 hp.

COMPARISON EXAMPLE C

A comparison process design, in which the crystalline paraxylene cakes from the separation devices that process the effluents of all three crystallization steps are combined and subjected to a reslurry operation (illustrated in FIG. 3), requires about 16% more refrigeration compressor power than the process of Example 2 for the same production rate of 115,840 lb/hr of paraxylene product having a purity of 99.90 wt % paraxylene. A feed containing 70 wt % paraxylene (stream 202) is sent to crystallizer 400 which operates at a temperature of 25° F. The crystallizer effluent, which comprises crystalline paraxylene and mother liquor, is sent to separation unit 217 comprising three centrifuges. The crystalline paraxylene cake from these centrifuges is dropped via line 205 into the reslurry drum 220. The reject filtrate (stream 204) is sent to crystallizer 500 which operates at 13° F. The effluent of paraxylene crystals and mother liquor from crystallizer 500 is sent to separation unit 218 comprising three centrifuges. The crystalline paraxylene cake from the centrifuges is dropped via line 208 into reslurry drum 220. The reject filtrate (stream 207) is sent to crystallizer 600 which operates at −5° F. The effluent from crystallizer 600 is sent to separation unit 219 comprising two centrifuges. The crystalline paraxylene cake from the centrifuges is dropped via line 211 into reslurry drum 220. The reject filtrate (stream 210) contains about 42 wt % paraxylene and is heat exchanged with the feed, stream 201, before being sent elsewhere in the unit. The slurry from the reslurry drum 220 is sent to separation unit 221 comprising three TNO hydraulic wash columns. These wash columns produce the entire 115,840 lb/hr of high purity paraxylene product which is collected via line 215. About 45% of the filtrate from the wash columns (stream 213) is sent via line 218 to the reslurry drum 220 to provide liquid for the reslurry operation. The reslurry drum operates at 42° F. The remaining filtrate from the wash columns is combined with stream 201 upstream of crystallizer 400. In this example, stream 214 does not exist. Three levels of propylene refrigeration are used in this example at pressures of about 48, 38 and 26 psia. The refrigeration compressor requires about 5178 hp, which is 15.5% higher than that for the design depicted in Example 6 (FIG. 2) and 6.0% higher than that for the design depicted in Example 5 (FIG. 1).

That which is claimed is:

1. A process for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting the liquid paraxylene product;

d) transferring at least a portion of filtrate from the first separation unit to a second crystallizer, which is operated at a temperature lower than that of the first crystallizer, crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature higher than that of the lowest temperature crystallizer;

i) separating the slurry mixture in a fourth separation unit to produce a filtrate and a crystalline paraxylene product, washing the paraxylene crystals with liquid paraxylene, completely melting the paraxylene crystals, and collecting the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

2. The process of claim 1 wherein the first crystallizer is operated at a temperature of about 30° F. to about 55° F.

3. The process of claim 1 wherein the first crystallizer is operated at a temperature of about 35° F. to about 45° F.

4. The process of claim 1 wherein the paraxylene-containing feedstream comprises at least about 75 wt % paraxylene.

5. The process of claim 1 wherein the paraxylene-containing feedstream comprises at least about 85 wt % paraxylene.

6. The process of claim 1 wherein the paraxylene-containing feedstream comprises at least about 90 wt % paraxylene.

7. The process of claim 1 wherein the second crystallizer is operated at a temperature of about −10° F. to about 35° F.

8. The process of claim 1 wherein the second crystallizer is operated at a temperature of about 15° F. to about 25° F.

9. The process of claim 1 wherein the third crystallizer is operated at a temperature of about −35° F. to about 5° F.

10. The process of claim 1 wherein the third crystallizer is operated at a temperature of about −10° F. to about −5° F.

11. The process of claim 1 wherein the crystalline paraxylene product from step (c) is combined with the crystalline paraxylene product from step (i) prior to melting.

12. The process of claim 11 wherein the combined paraxylene product comprises at least about 99.5 wt % paraxylene.

13. The process of claim 11 wherein the combined paraxylene product comprises at least about 99.7 wt % paraxylene.

14. The process of claim 11 wherein the combined paraxylene product comprises at least about 99.8 wt % paraxylene.

15. The process of claim 1 wherein the temperature of the slurry mixture in step (h) is about 10° F. to about 55° F.

16. The process of claim 1 wherein the temperature of the slurry mixture in step (h) is about 30° F. to about 50° F.

17. The process of claim 1 wherein the temperature of the slurry mixture in step (h) is about 38° F. to about 42° F.

18. The process of claim 1 wherein the temperature of the slurry mixture in step (h) is about 40° F. to about 42° F.

19. The process of claim 1 wherein the slurry mixture in step (h) comprises about 30 to about 60 weight percent crystalline paraxylene.

20. The process of claim 1 wherein the slurry mixture in step (h) comprises about 30 to about 50 weight percent crystalline paraxylene.

21. The process of claim 1 wherein the slurry mixture in step (h) comprises about 35 to about 50 weight percent crystalline paraxylene.

22. A process according to claim 1 for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of about −10° F. to about 35° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of about −35° F. to about 5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of about 10° F. to about 55° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

23. The process of claim 22 wherein the crystalline paraxylene product from step (c) is combined with the crystalline paraxylene product from step (i) prior to melting.

24. The process of claim 22 wherein the paraxylene-containing feedstream comprises at least about 75 wt % paraxylene.

25. The process of claim 22 wherein the paraxylene-containing feedstream comprises at least about 85 wt % paraxylene.

26. The process of claim 22 wherein the paraxylene-containing feedstream comprises at least about 90 wt % paraxylene.

27. A process according to claim 1 for the production of paraxylene from a paraxylene-containing feedstream comprising $C_8$ aromatic hydrocarbons and having a paraxylene concentration of at least about 60 weight percent, the process comprising:

a) crystallizing said feedstream in a first crystallizer at a temperature of about 30° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of about 15° F. to about 25° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer which is operated at a temperature of about −10° F. to about −5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of about 30° F. to about 50° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the second crystallizer; and k) recycling at least another portion of filtrate selected from the group consisting of filtrate from the first separation unit, filtrate from the fourth separation unit, and filtrate from the first and fourth separation units to the slurry apparatus.

28. The process of claim 27 wherein the crystalline paraxylene product from step (c) is combined with the crystalline paraxylene product from step (i) prior to melting.

29. The process of claim 27 wherein the paraxylene-containing feedstream comprises at least about 75 wt % paraxylene.

30. The process of claim 27 wherein the paraxylene-containing feedstream comprises at least about 85 wt % paraxylene.

31. The process of claim 27 wherein the paraxylene-containing feedstream comprises at least about 90 wt % paraxylene.

32. A process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting the liquid paraxylene product;

d) transferring at least a portion of filtrate from the first separation unit to a second crystallizer which is operated at a temperature lower than that of the first crystallizer, crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature lower than that of the second crystallizer, crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature higher than that of the lowest temperature crystallizer;

i) separating the slurry mixture in a fourth separation unit to produce a filtrate and a crystalline paraxylene product, washing the paraxylene crystals with liquid paraxylene, completely melting the paraxylene crystals, and collecting the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

33. The process of claim 32 wherein the crystalline paraxylene product from step (c) is combined with the crystalline paraxylene product from step (i) prior to melting.

34. The process of claim 33 wherein the combined paraxylene product comprises at least about 99.5 wt % paraxylene.

35. The process of claim 33 wherein the combined paraxylene product comprises at least about 99.7 wt % paraxylene.

36. The process of claim 33 wherein the combined paraxylene product comprises at least about 99.8 wt % paraxylene.

37. The process of claim 32 wherein the paraxylene-containing feedstream comprises at least about 75 wt % paraxylene.

38. The process of claim 32 wherein the paraxylene-containing feedstream comprises at least about 85 wt % paraxylene.

39. The process of claim 32 wherein the paraxylene-containing feedstream comprises at least about 95 wt % paraxylene.

40. The process of claim 32 wherein the temperature of the slurry mixture in step (h) is about 35° F. to about 45° F.

41. The process of claim 32 herein the temperature of the slurry mixture in step (h) is about 40° F. to about 42° F.

42. The process of claim 32 wherein the slurry mixture in step (h) comprises about 30 to about 60 weight percent crystalline paraxylene.

43. The process of claim 32 wherein the slurry mixture in step (h) comprises about 45 to about 55 weight percent crystalline paraxylene.

44. The process of claim 34 wherein the first crystallizer is operated at a temperature of about 30° F. to about 55° F.

45. The process of claim 34 wherein the first crystallizer is operated at a temperature of about 35° F. to about 45° F.

46. The process of claim 34 wherein the second crystallizer is operated at a temperature of about −10° F. to about 35° F.

47. The process of claim 34 wherein the second crystallizer is operated at a temperature of about 15° F. to about 25° F.

48. The process of claim 34 wherein the third crystallizer is operated at a temperature of about −35° F. to about 5° F.

49. The process of claim 34 wherein the third crystallizer is operated at a temperature of about −10° F. to about −5° F.

50. The process of claim 34 wherein the temperature of the slurry mixture in step (h) is about 10° F. to about 55° F.

51. The process of claim 34 wherein the temperature of the slurry mixture in step (h) is about 30° F. to about 50° F.

52. The process of claim 34 wherein the temperature of the slurry mixture in step (h) is about 38° F. to about 42° F.

53. The process of claim 34 wherein the slurry mixture in step (h) comprises about 30 to about 60 weight percent crystalline paraxylene.

54. The process of claim 34 wherein the slurry mixture in step (h) comprises about 30 to about 50 weight percent crystalline paraxylene.

55. The process of claim 34 wherein the slurry mixture in step (h) comprises about 35 to about 50 weight percent crystalline paraxylene.

56. The process of claim 1 wherein the amount of paraxylene crystals in the slurry mixture formed in the slurry apparatus is greater than the amount of paraxylene crystals sent to the slurry apparatus.

57. The process of claim 34 wherein the amount of paraxylene crystals in the slurry mixture formed in the slurry apparatus is greater than the amount of paraxylene crystals sent to the slurry apparatus.

58. A process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of about 10° F. to about 55° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of about −10° F. to about 35° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of about −35° F. to about 5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of about 10° F. to about 55° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

59. The process of claim 58 wherein the crystalline paraxylene product from step (c) is combined with the crystalline paraxylene product from step (i) prior to melting.

60. A process for the production of paraxylene from a paraxylene-containing feedstream comprising $C_8$ aromatic hydrocarbons and having a paraxylene concentration of at least about 55 weight percent, the process comprising:

a) crystallizing said feedstream in a first crystallizer at a temperature of about 20° F. to about 30° F.;

b) recovering an effluent comprising paraxylene crystals in a mother liquor;

c) separating the paraxylene crystals from the mother liquor in a first separation unit, washing the paraxylene crystals with liquid paraxylene, completely melting the paraxylene crystals, and collecting liquid paraxylene product;

d) transferring at least a portion of filtrate from the first separation unit to a second crystallizer which is operated at a temperature of about 5° F. to about 15° F., crystallizing the filtrate, and recovering an effluent comprising paraxylene crystals in a mother liquor;

e) separating the paraxylene crystals from the mother liquor in a second separation unit and sending the paraxylene crystals to a slurry apparatus;

f) transferring at least a portion of filtrate from the second separation unit to a third crystallizer, which is operated at a temperature of about −10° F. to about −5° F., crystallizing the filtrate, and recovering an effluent comprising paraxylene crystals in a mother liquor;

g) separating the paraxylene crystals from the mother liquor in a third separation unit and sending the paraxylene crystals to the slurry apparatus;

h) contacting the paraxylene crystals in the slurry apparatus with paraxylene-containing liquid to form a slurry mixture having a temperature of about 30° F. to about 50° F.;

i) separating the slurry mixture in a fourth separation unit to produce a filtrate and a crystalline paraxylene product, washing the paraxylene crystals with liquid paraxylene, completely melting the paraxylene crystals, and withdrawing the liquid paraxylene product;

j) recycling at least a portion of filtrate from the fourth separation unit to the first crystallizer; and k) recycling at least another portion of filtrate selected from the group consisting of filtrate from the first separation unit, filtrate from the fourth separation unit, and filtrate from the first and fourth separation units to the slurry apparatus.

61. The process of claim 52 wherein the crystalline paraxylene product from step (c) is combined with the crystalline paraxylene product from step (i) prior to melting 62. The process of claim 61 wherein the paraxylene-containing feedstream comprises at least about 75 wt % paraxylene.

63. The process of claim 61 wherein the paraxylene-containing feedstream comprises at least about 85 wt % paraxylene.

64. The process of claim 61 wherein the paraxylene-containing feedstream comprises at least about 95 wt % paraxylene.

65. The process of claim 61 wherein the temperature of the slurry mixture in step (h) is about 40° F. to about 42 F.

66. The process of claim 61 wherein the slurry mixture in step (h) comprises about 30 to about 60 weight percent paraxylene.

* * * * *

UNITED STATES PATENT AND TRADEMARK OFFICE
CERTIFICATE OF CORRECTION

PATENT NO. : 6,565,653 B2
DATED : May 20, 2003
INVENTOR(S) : Richard A. Wilsak

It is certified that error appears in the above-identified patent and that said Letters Patent is hereby corrected as shown below:

<u>Column 28,</u>
Line 12, reads "The process of Claim 32 herein the temperature" should read
-- The process of Claim 32 wherein the temperature --
Line 19, reads "The process of Claim 34 wherein the first crystallizer" should read
-- The process of Claim 32 wherein the first crystallizer --
Line 21, reads "The process of Claim 34 wherein the first crystallizer" should read
-- The process of Claim 32 wherein the first crystallizer --
Lines 23-24, reads "The process of Claim 34 wherein the second crystallizer" should read -- The process of Claim 32 wherein the second crystallizer --
Lines 26-27, reads "The process of Claim 34 wherein the second crystallizer" should read -- The process of Claim 32 wherein the second crystallizer --
Line 29, reads "The process of Claim 34 wherein the third crystallizer" should read
-- The process of Claim 32 wherein the third crystallizer --
Line 31, reads "The process of Claim 34 wherein the third crystallizer" should read
-- The process of Claim 32 wherein the third crystallizer --
Lines 33-34, reads "The process of Claim 34 wherein the temperature of the slurry" should read -- The process of Claim 32 wherein the temperature of the slurry --
Line 34, reads "The process of Claim 34 wherein the temperature" should read
-- The process of Claim 32 wherein the temperature --
Lines 36-37, reads "The process of Claim 34 wherein the temperature of the slurry" should read -- The process of Claim 32 wherein the temperature of the slurry --
Line 38, reads "The process of Claim 34 wherein the slurry mixture in step (h)" should read -- The process of Claim 32 wherein the slurry mixture in step (h) --
Lines 41-42, reads "The process of Claim 34 wherein the slurry mixture in step (h)" should read -- The process of Claim 32 wherein the slurry mixture in step (h) --
Lines 44-45, reads "The process of Claim 34 wherein the slurry mixture in step (h)" should read -- The process of Claim 32 wherein the slurry mixture in step (h) --
Lines 51-52, reads "The process of Claim 34 wherein the amount of paraxylene" should read -- The process of Claim 32 wherein the amount of paraxylene --

UNITED STATES PATENT AND TRADEMARK OFFICE
CERTIFICATE OF CORRECTION

PATENT NO.    : 6,565,653 B2
DATED         : May 20, 2003
INVENTOR(S)   : Richard A. Wilsak It is certified that error appears in the above-identified patent and that said Letters Patent is hereby corrected as shown below:

Column 30,
Lines 34-35, reads "The process of Claim 52 wherein the crystalline paraxylene" should read -- The process of Claim 60 wherein the crystalline paraxylene --
Lines 37-38, reads "The process of Claim 61 wherein the paraxylene-containing" should read -- The process of Claim 60 wherein the paraxylene-containing --
Lines 40-41, reads "The process of Claim 61 wherein the paraxylene-containing" should read -- The process of Claim 60 wherein the paraxylene-containing --
Lines 43-44, reads "The process of Claim 61 wherein the paraxylene-containing" should read -- The process of Claim 60 wherein the paraxylene-containing --
Lines 46-47 reads "The process of Claim 61 wherein the temperature of the slurry" should read -- The process of Claim 60 wherein the temperature of the slurry --
Lines 49-50, reads "The process of Claim 61 wherein the slurry mixture in step (h)" should read -- The process of Claim 60 wherein the slurry mixture in step (h) --

Signed and Sealed this

Twenty-first Day of October, 2003

JAMES E. ROGAN
*Director of the United States Patent and Trademark Office*